United States Patent
Ash et al.

(10) Patent No.: US 8,751,251 B2
(45) Date of Patent: Jun. 10, 2014

(54) KEY NOTIFICATIONS IN A CLINICAL COMPUTING ENVIRONMENT

(75) Inventors: Michael A. Ash, Parkville, MO (US); John Q. DeVerter, Liberty, MO (US); Hal W. Schierts, Shawnee, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 1685 days.

(21) Appl. No.: 11/427,623

(22) Filed: Jun. 29, 2006

(65) Prior Publication Data

US 2008/0004502 A1   Jan. 3, 2008

(51) Int. Cl.
*G06Q 50/24*   (2012.01)
(52) U.S. Cl.
CPC .................................... *G06Q 50/24* (2013.01)
USPC ............................................................. 705/2
(58) Field of Classification Search
USPC ........................................................ 705/2–4
See application file for complete search history.

(56) References Cited

U.S. PATENT DOCUMENTS

| | | | |
|---|---|---|---|
| 5,942,986 A * | 8/1999 | Shabot et al. ................ 340/7.29 |
| 2004/0179430 A1 * | 9/2004 | Bahar et al. ..................... 368/10 |
| 2004/0193703 A1 * | 9/2004 | Loewy et al. .................. 709/220 |
| 2006/0004605 A1 * | 1/2006 | Donoghue et al. ................ 705/2 |
| 2006/0206011 A1 * | 9/2006 | Higgins et al. ................ 600/300 |
| 2006/0271410 A1 * | 11/2006 | Rosenfeld et al. ................ 705/3 |
| 2006/0282302 A1 * | 12/2006 | Hussain ........................... 705/9 |
| 2007/0040692 A1 * | 2/2007 | Smith et al. ................. 340/573.1 |
| 2008/0209046 A1 * | 8/2008 | Karkanias et al. ............ 709/227 |

* cited by examiner

*Primary Examiner* — John Pauls
(74) *Attorney, Agent, or Firm* — Shook, Hardy & Bacon LLP

(57) ABSTRACT

Automatic triaging of patient information within a clinical computing environment is provided. Items of patient information are received, and each item is compared against predefined criteria to determine whether the item is time-sensitive. If an item satisfies a threshold of time-sensitivity, a key notification is provided for the item. A clinician may receive the key notification regardless of the view or application in which the clinician is working. The clinician may directly navigate from the key notification to the associated information, access additional information if necessary, and resolve the condition. Additionally, clinicians may control the triaging of information by specifying patient populations and thresholds required to trigger key notifications.

15 Claims, 19 Drawing Sheets

FIG. 2.

TASK VIEW PATIENT CHART CLINIC SCHEDULE INBOX HELP

HOME  SCHEDULE  PATIENTS  INBOX  BASELINE WEST  POLICIES  GUIDELINES  PRINT  REPORTS       CHANGE USER     CRIT: 0 ABN: 1 DUE: 1

KOHLER, PAMELA  x                                                                              RECENT ▼ | NAME

KOHLER, PAMELA 66Y F   ALLERGIES: PENICILLINS, CODE...  VISIT REASON: FOLLOW-UP DM 2   ADVANCE DIRECTIVE: YES   IQHEALTH: YES   CHR: YES

MENU              ↕ OVERVIEW                                                                                                      0 MIN. AGO

OVERVIEW
REVIEW CHART              THIS VISIT         SINCE LAST TIME          SUMMARIES
PROBLEM & DIAGNOSIS
RESULTS REVIEW        STICKY NOTES
ALLERGIES      + ADD   WRITTEN BY          CREATED DATE/TIME        TEXT
ORDERS         + ADD   LOCKE, SUE          01/05/2005 11:30         UNIVERSITY OF MISSOURI ALUMNI
MEDICATIONS            << PREVIOUS | NEXT >>
HISTORY                COMMUNICATION FROM/ABOUT THIS PATIENT
DOCUMENTATION  + ADD   ITEMS               TYPE
HEALTH MAINTENANCE     DUE (2)             REFILL REQUESTS (1); REMINDER (1)
IMMUNIZATIONS          RESULTS (6)         ABNORMAL (1); NORMAL (5)
COMMUNICATE    + ADD   REMINDERS
DEMOGRAPHICS           PRIORITY            SHOW UP DATE/TIME ▽      SUBJECT                                          CREATED DATE/TIME    STATUS
                       ROUTINE             10/10/2005 14:00         ASK FOR COPY OF WEIGHT LOSS AND EXERCISE LOG     09/01/2005 09:23     OPENED
                       << PREVIOUS | NEXT >>

VISIT INFORMATION
                       SERVICE DATE/TIME ≡  ENCOUNTER TYPE  FACILITY         PROVIDER         VISIT REASON      DIAGNOSIS
                       10/10/2005 14:00     OUTPATIENT      BWMP FAM PRAC    JONES, JOHN MD   FOLLOW-UP DM2     DIABETES MELLITUS WITHOUT MEN...

REPORTED CHIEF COMPLAINT
                       PATIENT REPORTS SHE IS HERE FOR DIABETIC MANAGEMENT.

VITAL SIGNS / MEASUREMENT
                       TEMPERATURE ORAL          97.8 DEGF    10/10/2005 09:00   98.6 DEGF    04/04/2005 10:00
                       PERIPHERAL PULSE RATE     91 BPM       10/10/2005 09:00   80 BPM       04/04/2005 10:00
                       RESPIRATORY RATE          16 BR/MIN    10/10/2005 09:00   6 BR/MIN     04/04/2005 10:00
                       SYSTOLIC BLOOD PRESSURE   136 M MHG    10/10/2005 09:00   135 M MHG    04/04/2005 10:00
                       DIASTOLIC BLOOD PRESSURE  86 M MHG     10/10/2005 09:00   86 M MHG     04/04/2005 10:00

TASK VIEW PATIENT CHART CLINIC SCHEDULE INBOX HELP

HOME  SCHEDULE  PATIENTS  INBOX  BASELINE WEST  POLICIES  GUIDELINES  PRINT  REPORTS

KOHLER, PAMELA  ✕

KOHLER, PAMELA 66Y F    ALLERGIES: PENICILLINS, CODE...    VISIT REASON: FOLLOW-UP DM 2    ADVANCE DIRECTIVE: YES    IQHEALTH: YES    CHANGE USER

RECENT ▼    CHR: YES    CRIT: 0  ABN: 1  DUE: 1
DUE: SMITH, BOB

MENU — 602
OVERVIEW
REVIEW CHART
PROBLEM & DIAGNOSIS
RESULTS REVIEW
ALLERGIES        + ADD
ORDERS           + ADD
MEDICATIONS
HISTORY
DOCUMENTATION    + ADD
HEALTH MAINTENANCE
IMMUNIZATIONS
COMMUNICATE      + ADD
DEMOGRAPHICS

OVERVIEW

| THIS VISIT | SINCE LAST TIME | SUMMARIES |

STICKY NOTES

| WRITTEN BY | CREATED DATE/TIME | TEXT |
| LOCKE, SUE | 01/05/2005 11:30 | UNIVERSITY OF MISSOURI ALUMNI |

<< PREVIOUS | NEXT >>

COMMUNICATION FROM/ABOUT THIS PATIENT

| ITEMS | TYPE |
| DUE (2) | REFILL REQUESTS (1); REMINDER (1) |
| RESULTS (6) | ABNORMAL (1); NORMAL (5) |

REMINDERS

| PRIORITY | SHOW UP DATE/TIME ▼ | SUBJECT | CREATED DATE/TIME | STATUS |
| ROUTINE | 10/10/2005 14:00 | ASK FOR COPY OF WEIGHT LOSS AND EXERCISE LOG | 09/01/2005 09:23 | OPENED |

<< PREVIOUS | NEXT >>

VISIT INFORMATION

| SERVICE DATE/TIME ▼ | ENCOUNTER TYPE | FACILITY | PROVIDER | VISIT REASON | DIAGNOSIS |
| 10/10/2005 14:00 | OUTPATIENT | BWMP FAM PRAC | JONES, JOHN MD | FOLLOW-UP DM2 | DIABETES MELLITUS WITHOUT MEN... |

REPORTED CHIEF COMPLAINT
PATIENT REPORTS SHE IS HERE FOR DIABETIC MANAGEMENT.

VITAL SIGNS / MEASUREMENT

| TEMPERATURE ORAL | 97.8 DEGF | 10/10/2005 09:00 | | 98.6 DEGF | 04/04/2005 10:00 |
| PERIPHERAL PULSE RATE | 91 BMP | 10/10/2005 09:00 | | 80 BPM | 04/04/2005 10:00 |
| RESPIRATORY RATE | 16 BR/MIN | 10/10/2005 09:00 | | 6 BR/MIN | 04/04/2005 10:00 |
| SYSTOLIC BLOOD PRESSURE | 136 M MHG | 10/10/2005 09:00 | | 130 M MHG | 04/04/2005 10:00 |
| DIASTOLIC BLOOD PRESSURE | 86 M MHG | 10/10/2005 09:00 | | 86 M MHG | 04/04/2005 10:00 |

0 MIN. AGO 604
606

| TASK VIEW PATIENT CHART CLINIC SCHEDULE INBOX HELP |
|---|
| ⌂ HOME 📅 SCHEDULE 👤 PATIENTS ✉ INBOX ⋮⋮⋮ BASELINE WEST 📋 POLICIES 📋 GUIDELINES ⋮⋮⋮ PRINT 📊 REPORTS 🔄 CHANGE USER |

KOHLER, PAMELA  ✕                                                             ⋮⋮⋮ CRIT: 0 ABN: 1 DUE: 0

SCHEDULE

DATE: 10/10/2005 ▼                                       RESOURCE: JONES, JOHN MD ▼

| TIME | APPOINTMENT TYPE | NAME | DURATION | DESCRIPTION | STATUS | ROOM # |
|---|---|---|---|---|---|---|
| 0900 | NEW PATIENT | ROPER, SARAH | 00:30 | KNEE PAIN | CHECKED OUT | |
| 15 | | | | | | |
| 30 | ESTABLISHED PATIENT | GILMORE, GWEN S. | 00:30 | WELL WOMAN EXAM | CHECKED OUT | |
| 45 | | | | | | |
| 1000 | CONSULT | MURPHY, FRED S. | 00:30 | CARDIO | CHECKED IN | |
| 15 | | | | | | |
| 30 | FOLLOWUP | KOHLER, PAMELA | 00:30 | FOLLOW-UP DIABETES | CHECKED IN | EXAM ROOM 1 |
| 1100 | ESTABLISHED PATIENT | BARONIAN, ELLA | 00:30 | EAR PAIN | CHECKED IN | EXAM ROOM 2 |
| 15 | | | | | | |
| 30 | ESTABLISHED PATIENT | KROUSEM JANE S. | 00:30 | RECTAL BLEEDING | CONFIRMED | |
| 45 | | | | | | |
| 1200 | | | | | | |
| 15 | | | | | | |
| 30 | | | | | | |
| 45 | | | | | | |
| 1300 | ESTABLISHED PATIENT | SANDERS, JAIME | 00:30 | EAR PAIN | CONFIRMED | |
| 15 | | | | | | |
| 30 | ESTABLISHED PATIENT | JOHNSON, BRANDON | 00:30 | 1 WEEK CHECK | CONFIRMED | |
| 45 | | | | | | |
| 1400 | FOLLOWUP | JONES, VICTOR | 00:30 | FOLLOW-UP HYPERTENSION | CONFIRMED | |
| 15 | | | | | | |
| 30 | FOLLOWUP | DOORMAN, DAVID | 00:30 | KNEE PAIN | RESCHEDULED | |
| 45 | | | | | | |
| 1500 | ESTABLISHED PATIENT | COLDWATER, DAVID | 00:30 | TROUBLE BREATHING | CONFIRMED | |
| 15 | | | | | | |
| 30 | ESTABLISHED PATIENT | HILL, MARY | 00:30 | PALPITATIONS | CONFIRMED | |
| 45 | | | | | | |
| 1600 | FOLLOWUP | PETERSON, JENN | 00:30 | FOLLOW-UP | CONFIRMED | |
| 15 | | | | | | |

INBOX

TASK  VIEW  PATIENT  CHART  CLINIC  SCHEDULE  INBOX  HELP

HOME | SCHEDULE | PATIENTS | INBOX | BASELINE WEST | POLICIES | GUIDELINES | PRINT | REPORTS | CHANGE USER

KOHLER, PAMELA  ×                           CANYON, BILL ▼    RECENT ▼   NAME    CRIT: 0  ABN: 1  DUE: 0

DISPLAY: LAST 30 DAYS ▼   INBOX | PROXIES | POOLS                                                  0 MIN. AGO

- PRIORITY ITEMS (0)
- DUE (0)
- INBOX ITEMS (15)
  - RESULTS (10)
    - CRITICAL (1)
    - NORMAL (9)
  - DOCUMENTS (1)
    - DOCUMENTS TO SIGN (1)
  - MESSAGES (4)
    - GENERAL MESSAGES (2)
    - REFILL REQUESTS (2)
    - MESSAGES FROM PATIENT
    - CC MESSAGES
  - ORDERS (0)
- WORK ITEM (0)
- NOTIFICATIONS (35)
  - NOTIFY RECEIPTS (35)
  - SENT ITEMS
  - MESSAGING TRASH

RESULTS - ABNORMAL | RESULTS TO ENDORSE: CANYON...

NEW | DELETE | REPLY | REPLY ALL | FORWARD | MESSAGE JOURNAL

CANYON, BILL 59Y M
DOB: 10/10/1945  MRN: 00-00-0989  FIN: 005436  ALLERGIES: NKA  VISIT REASON: FOLLOW UP  ADVANCE DIRECTIVE: YES  IQHEALTH: YES  CHR: YES
LOCATION: BW8E: 8E 05:0  VISIT DATE: 10/10/2005  PCP: JOHN JONES, MD  CLINICAL TRIAL: NO

| DATE | ITEM | VALUE | REFERENCE RANGE | TREND |
|---|---|---|---|---|
| 10/10/2005 06:00 | SODIUM LEVEL | 139 mEq/L | 135.0 - 145.0 | TREND... |
| | POTASSIUM LEVEL | L 3.4 mEq/L | 3.5 - 5.0 | HIDE... |
| | CHLORIDE | 107 mEq/L | 95.0 - 110.0 | TREND... |
| | CO2 | 26 mEq/L | 22.0 - 33.0 | TREND... |
| | AGAP | 9 mEq/L | 6.0 - 16.0 | TREND... |
| | BUN | 14 mg/dL | 4.0 - 18.0 | TREND... |
| | CREATINE | 1 mg/dL | 0.5 - 1.2 | HIDE... |
| | GLUCOSE RANDOM | 90 mg/dL | 65.0 - 110.0 | TREND... |
| | CALCIUM LEVEL | 9 mg/dL | 9.0 - 10.6 | TREND... |

SEARCHING INCREMENTS OF FIVE FOR LAST 24 MONTHS
GROUP BY: ● RESULTS  ○ DATE/TIME    CLEAR RESULTS

| DATE/TIME | VALUE |
|---|---|
| POTASSIUM | |
| 02/25/2005 08:00 | 4.0 mEq/L |
| 08/21/2004 10:00 | 4.1 mEq/L |
| 03/22/2004 09:00 | 4.2 mEq/L |
| 09/22/2003 09:00 | 4.1 mEq/L |
| 01/20/2003 09:00 | 4.2 mEq/L  MORE... |
| CREATINE | |
| 02/25/2005 08:00 | 1.1 mEq/dL |
| 08/21/2004 10:00 | 1.0 mEq/dL |
| 03/22/2004 09:00 | 0.9 mEq/dL |
| 09/22/2003 09:00 | 1.0 mEq/dL |
| 01/20/2003 09:00 | 1.0 mEq/dL  MORE... |

● ENDORSE

ADDITIONAL FORWARD ACTION
CALL PATIENT FOR FOLLOWUP ▼    TO  RED NURSING POOL ▼

ADDITIONAL FORWARD ACTION
▼    TO  ▼

○ REFUSE  ← 718

REASON ▼

COMMENTS (120 CHARACTER LIMIT)
TELL PATIENT TO EAT A FEW BANANAS AND REPEAT LAB.

OK          OK & NEXT

| TASK VIEW PATIENT CHART CLINIC SCHEDULE INBOX HELP | | |
|---|---|---|
| ⌂ HOME 📅 SCHEDULE 👥 PATIENTS ⋮⋮⋮ BASELINE WEST 📖 POLICIES 📗 GUIDELINES ⋮⋮ PRINT 📊 REPORTS 👤 CHANGE USER | | ⚠ CRIT: 1 ABN: 0 DUE: 0 |
| KOHLER, PAMELA  × | MURPHY, FRED ▼ | 🔍 NAME ▼ |

INBOX

| INBOX | PROXIES | POOLS | | | | | | 🔄 1 MIN. AGO |
|---|---|---|---|---|---|---|---|---|
| DISPLAY: LAST 30 DAYS ▼ ... | | | | | | | | |

| | RESULTS - CRITICAL | RESULTS TO ENDORSE: MURPHY... ⟶ 816 | | | |
|---|---|---|---|---|---|
| ⊞ PRIORITY ITEMS (0) | 📩 NEW 📂 OPEN 🗑 DELETE ↩ REPLY ✉ REPLY ALL ➡ FORWARD ✉ MESSAGE JOURNAL ⇦ PREVIOUS ⇨ NEXT | | | | |
| ⊞ DUE (0) | MURPHY, FRED 59Y M ALLERGIES: NKA VISIT REASON: FOLLOW UP ADVANCE DIRECTIVE: YES IQHEALTH: YES CHR: YES | | | | |
| ⊞ INBOX ITEMS (15) | DOB: 10/10/1945 MRN: 00-00-0435 FIN: 0/5432 LOCATION: BW7E; 7E 05; 0 VISIT DATE: 10/10/2005 PCP: JOHN JONES, MD CLINICAL TRIAL: NO | | | | |
| ⊟ RESULTS (10) | DATE | ITEM | VALUE | REFERENCE RANGE | |
| [CRITICAL (1)] ---- | ☑ 10/10/2005 09:25 | ☑ WBC | 9.2 L/mm3 | 3.8 - 10.2 | TREND... |
| NORMAL (9) | | ☑ RBC | 139 mEq/L | 4.34 - 5.57 | TREND... |
| ⊟ DOCUMENTS (1) | | ☑ HGB | 7.6C gm/dL | 13.3 - 16.7 | TREND... |
| DOCUMENTS TO SIGN (1) | | ☑ HCT  ⟵820 | L 2.41% | 39.2 - 49.2 | TREND... ⟵822 |
| ⊟ MESSAGES (4) | | ☑ MCV | 82.22 unit/m3 | 80.0 - 97.0 | TREND... |
| GENERAL MESSAGES (2) | | ☑ MCH | 26.6pg/mL | 26.0 - 33.0 | TREND... |
| REFILL REQUESTS (2) | | ☑ MCHC | L 32.3% | 32.6 - 36.0 | TREND... |
| MESSAGES FROM PATIENT | | ☑ RDW | H 19.3% | 11.4 - 13.6 | TREND... |
| CC MESSAGES | | ☑ PLT | 259 1000uL | 139-400 | TREND... |
| ⊟ ORDERS (0) | | ☑ MPV | 10.0 | 6.6 - 10.1 | TREND... |
| ⊞ WORK ITEM (0) | | | | | |
| ⊞ NOTIFICATIONS (35) | ADDITIONAL FORWARD ACTION | | | | |
| NOTIFY RECEIPTS (35) | ⦿ ENDORSE [_____] TO [_____] | | | | |
| SENT ITEMS | ADDITIONAL FORWARD ACTION | | | | |
| MESSAGING TRASH | ○ REFUSE ⟵818 | | | | |
| | REASON [_____] ▼ TO [_____] | | | | |
| | | | | COMMENTS (120 CHARACTER LIMIT) | |
| | | | | [_____] | |
| | | | | [  OK  ] [ OK & NEXT ] | |

KEY NOTIFICATIONS IN A CLINICAL COMPUTING ENVIRONMENT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Triaging of information in a clinical setting, such as a physician office, is typically a manual process. Information to be reviewed by a physician may be placed in specific locations throughout a physician office or otherwise delivered to the physician depending upon the criticality of the information. For example, less time-sensitive and less critical information may be placed at a physician's desk, such that the physician may review the information at a convenient time. More time-sensitive information may be located at a strategic location, such as next to an exam room or a nurses' station, so that a physician may timely review the information and address any needs in between seeing patients. Highly critical and time-sensitive results, such as critical results from laboratory or diagnostic tests indicating a potentially life-threatening condition for a patient, may result in the physician being interrupted by a nurse or a page received via a pager.

The end-to-end process of notifying a physician of critical and time-sensitive information may often be slow and inefficient. For example, in the context of notifying a physician of a critical laboratory result, the process may begin when a laboratory technician obtains a result and interprets it as a critical result. The technician may determine where the patient is located, and call a ward clerk or receptionist at the patient location. The nurse responsible for the patient may then be located and provided the critical information. After receiving the critical information, the nurse may pull the patient's chart and chart the information. The nurse may then need to review policies and procedures to determine how to deliver the information to the appropriate physician (e.g., call a pager or answering service). In cases in which the physician is seeing a patient and receives a page, the physician may interrupt the exam to return the page. After receiving the critical information, the physician will typically need to decide how to address the situation. Often, the physician requires additional information, such as previous testing values, to make such a determination. However, the nurse or laboratory providing the critical information to the physician may not have such additional information readily available. In such cases, the physician must obtain the necessary information and then make a determination regarding how to address the critical information.

Accordingly, current approaches to triaging information present a number of drawbacks. As indicated, the process may often be time-consuming for cases in which time is of the essence. In addition, a manual approach to delivering such information may be error-prone as it provides opportunities for the miscommunication of information. Further, when a physician receives the information, additional background information may not be readily available to allow the physician to make an immediate decision. Moreover, the physician has little control over the triaging of information as the initial interpretation of information and determination of the criticality of the information is left to others. As such, physicians may be needlessly interrupted for notifications of information deemed to be critical or highly time-sensitive by others, but which is in fact less time-sensitive information.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to triaging patient information in a clinical setting by providing key notifications for time-sensitive items and allowing clinicians to access and address the time-sensitive items via the key notifications. Accordingly, in one aspect, an embodiment of the present invention is directed to a method in a clinical computing environment for automatically triaging one or more items of patient information. The method includes receiving the one or more items of patient information. The method also includes identifying at least one of the one or more items of patient information as a time-sensitive item. The method further includes presenting a key notification for the time-sensitive item.

In another aspect of the invention, an embodiment is directed to a system in a clinical computing environment for automatically triaging one or more items of patient information. The system includes an item receiving component, an identification component, and a key notification component. The item receiving component is capable of receiving the one or more items of patient information. The identification component is capable of identifying at least one of the one or more items of patient information as a time-sensitive item. The key notification component is capable of presenting a key notification for the time-sensitive item.

Yet another embodiment of the invention is directed to one or more computer-readable media having computer-useable instructions embodied thereon that provide for the presentation of one or more user interfaces for triaging patient information. The one or more user interfaces include a key notification area configured to display one or more key notifications. Each key notification may correspond with one or more items of patient information determined to satisfy predefined criteria.

BRIEF DESCRIPTION OF THE SEVERAL VIEWS OF THE DRAWINGS

The present invention is described in detail below with reference to the attached drawing figures, wherein:

FIG. 2 is an illustrative screen display showing an exemplary key notification user interface provided when a user is viewing an organizer home page in accordance with an embodiment of the present invention;

FIG. 3 is an illustrative screen display showing an exemplary key notification user interface provided when a user is viewing a patient chart in accordance with an embodiment of the present invention;

FIGS. 6A-6D are illustrative screen displays showing a clinician receiving a key notification for a due item and addressing the due item in accordance with an embodiment of the present invention;

FIGS. 7A-7E are illustrative screen displays showing a clinician receiving a key notification for an abnormal item and addressing the abnormal item in accordance with an embodiment of the present invention; and FIGS. 8A-8E are illustrative screen displays showing a clinician receiving a key notification for a critical item and addressing the critical item in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods, systems, and user interfaces for the automatic triaging of information by providing electronic notifications of key information. In accordance with embodiments of the present invention, a clinician may receive key notifications, for example via a clinical computing system, regardless of the view or application in which the clinician may be working, thereby providing a timely notification of such key information. The clinician may directly navigate from a key notification to the associated information, access additional information if necessary, and resolve the condition. Additionally, embodiments of the present invention provide clinicians with control over the triaging of information by allowing clinicians to specify patient populations and thresholds required to trigger key notifications. Having described a brief overview of embodiments of the present invention, an exemplary operating environment is described below.

Figure 1:
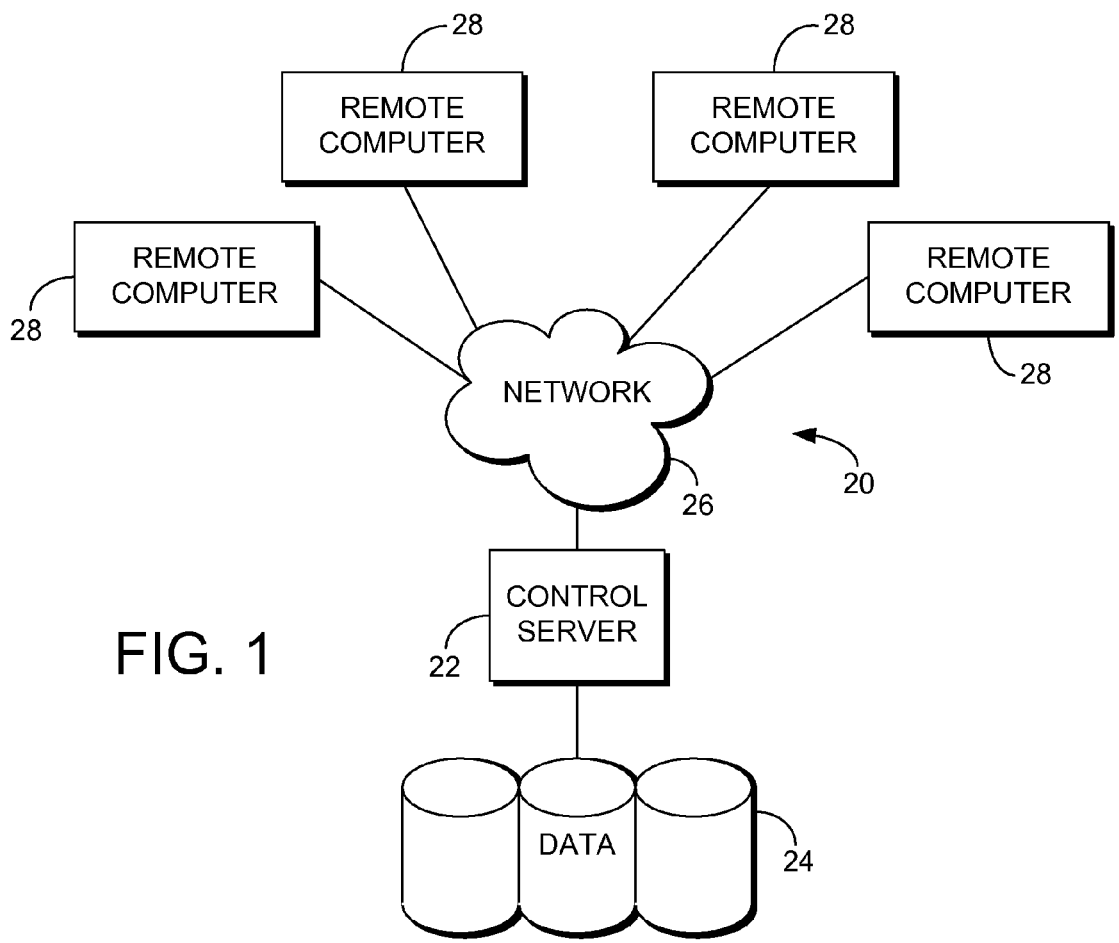
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

As previously indicated, embodiments of the present invention are directed to automatically triaging information in clinical settings by communicating electronic key notifications to clinicians. Key notifications are provided for items deemed to be of higher criticality and/or of a more time-sensitive nature based on predetermined criteria. The predetermined criteria may be system-defined and/or user-defined within various embodiments of the present invention as described in further detail below. By way of example only and not limitation, key notifications may be provided for abnormal and critical items, such as results and information from laboratory tests, diagnostic tests (e.g., CAT scans, x-rays, etc.), and the like. As known in the art, results and information are deemed critical when they present a condition that may be life-threatening to a patient or that otherwise dictates immediate attention by a physician. Abnormal results and information include results that are outside of a defined range or information that otherwise deviates from a defined norm, but which does not rise to the level of criticality requiring a physician's immediate attention. Additionally, key notifications may be provided for policy or procedure action items that are becoming due (e.g., a patient requiring a refill prescription for a medication by a particular time).

Figure 2:
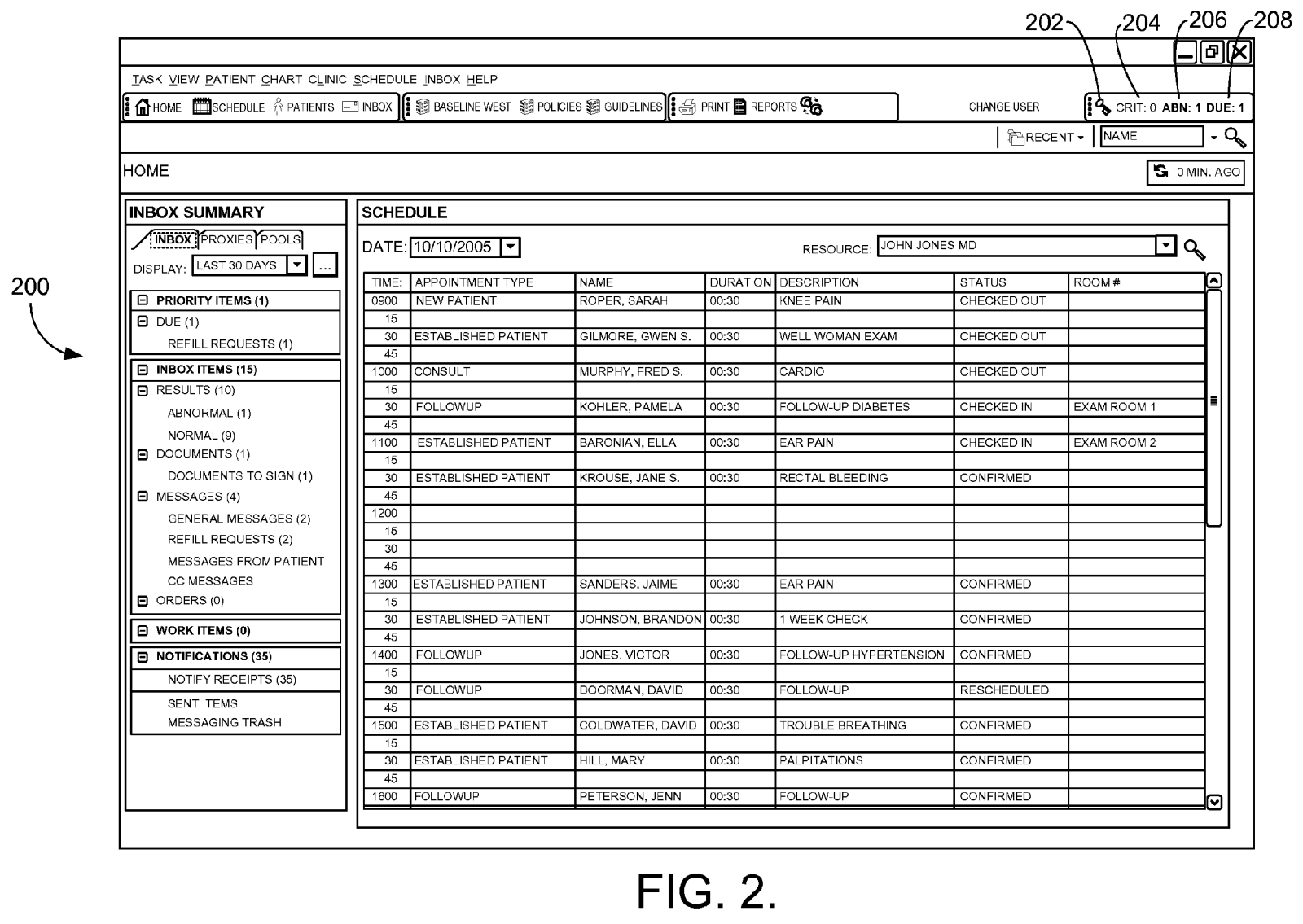

Referring to FIG. 2, a screen display 200 is illustrated showing an exemplary key notification user interface 202 in accordance with an embodiment of the present invention. As shown in FIG. 2, the key notification user interface 202 provides an indication of critical items 204, abnormal items 206, and due items 208 received for a clinician. Additionally, the key notification user interface 202 includes a counter for each type of key notification to indicate the number of unaddressed items within each category. For example, the key notification user interface 202 indicates that there are currently no critical items, one abnormal item, and one due item.

Key notifications may be provided to a clinician regardless of the view or application in which the clinician may be currently working. For example, the key notification user interface 202 shown in FIG. 2 is provided while a clinician is within an organizer home page. As another example, in FIG. 3, a key notification user interface 302 is provided while a clinician is viewing a patient's chart. It should be further noted that key notifications may be provided independently of any patient information currently being viewed by a clinician. For example, in FIG. 3, the clinician is viewing the patient chart for the patient, Pamela Kohler. However, the key notifications provided via the key notification user interface 302 in FIG. 3 are in no way limited to items for Pamela Kohler, but may include items for any patient within a predefined pool for the clinician. Furthermore, although key notification user interfaces are shown in FIG. 2 and FIG. 3 as integrated within an application, in some embodiments a key notification user interface may be provided independent of any application, such as via an independent pop-up window, for example.

Various embodiments of the present invention may employ a number of different ways of directing a clinician's attention to key notifications when they are received. For example, in some embodiments, a visual alert, such as a flashing indication, may be provided to direct the clinician's attention to a key notification. In some embodiments, an audible alert may be provided when a key notification is received, thereby directing the clinician's attention to the key notification. Such an audible alert may be useful, for example, in situations in which a clinician has access to a computing device in an exam room. The clinician may receive a key notification while his/her attention is not directed to the computing device (e.g., when the clinician is physically examining a patient). In such cases, the clinician may hear the audible alert, recognize that the sound is associated with a key notification, and direct his/her attention to the key notification. Other types of alerts may also be provided within the scope of the present invention, such as a vibrating alert provided for a portable computing device.

As noted above, key notifications are provided only for items that meet predefined criteria indicating that the items meet a sufficient level of criticality and time-sensitivity. In some embodiments, the predefined criteria may be based at least in part on patient populations. In other words, items may be filtered for key notifications based on patient populations. For example, a clinician may have thousands of patients. The patients may fall into a variety of categories, such as chronic patients, hospitalized patients, and clinical trial patients, for example. The clinician may only desire key notifications for a subset of the different patient populations, thereby excluding items associated with some patients. Accordingly, only items associated with certain patients are considered for key notifications. In some embodiments, this may entail providing a predetermined list of patients for which key notifications may be provided. In other embodiments, this may entail providing a predetermined list of patients for which key notifications may not be provided. In further embodiments, this may entail defining patient characteristics (e.g., type of patient) that will dictate whether items associated with different patients may be included for key notifications.

In some embodiments, multiple sets of key notifications may be provided for a clinician based on different patient populations. For example, a clinician may wish to have one set of key notifications provided for clinical trial patients and another set of key notifications provided for the remainder of the clinician's patients. In such embodiments, multiple key notification user interfaces may be provided, each corresponding with a particular patient population. Indicia may be provided with each key notification user interface such that the clinician may readily recognize the patient population associated with each user interface. In further embodiments, a patient specific key notification user interface may be provided corresponding with a patient chart a user is viewing.

The predefined criteria used to determine items for key notifications may further include system-defined and/or user-defined thresholds for criticality and time-sensitivity. In some embodiments, thresholds may be system-defined based on standard practices within the healthcare industry or within a particular clinical facility or healthcare system. For example, a standard practice may dictate that a range of values are considered normal for a particular laboratory test. Certain values outside of that range may be considered abnormal, and extreme values may be considered critical. Accordingly, such values dictated by the standard practice may be used as thresholds for the purposes of determining items for key notifications.

There are numerous situations in which a user may wish to control the thresholds for key notifications. Accordingly, in some embodiments of the present invention, user-defined thresholds may be set to deviate from standard practices and system-defined thresholds. For example, cases arise in which items may be deemed abnormal or critical based on standard practices, but are normal in light of additional information. For instance, a patient that has renal failure and receives kidney dialysis will typically have laboratory results (e.g., for creatinine) that are abnormal for a normal patient. However, the results may be normal for such a patient with renal failure. In such cases, a clinician may wish to override system-defined thresholds and set user-define thresholds appropriate in light of the patient's condition.

Some user-defined thresholds may be global thresholds that are applied at a practice level. For example, a user may define thresholds for particular sets of laboratory test results for all patients having renal failure. Other user-defined thresholds may be patient-specific. For example, a user may set thresholds for a particular patient based on the patient's condition. Moreover, a single user-defined threshold may consist of multiple rules for determining whether a key notification should be provided for a particular item.

Figure 4:
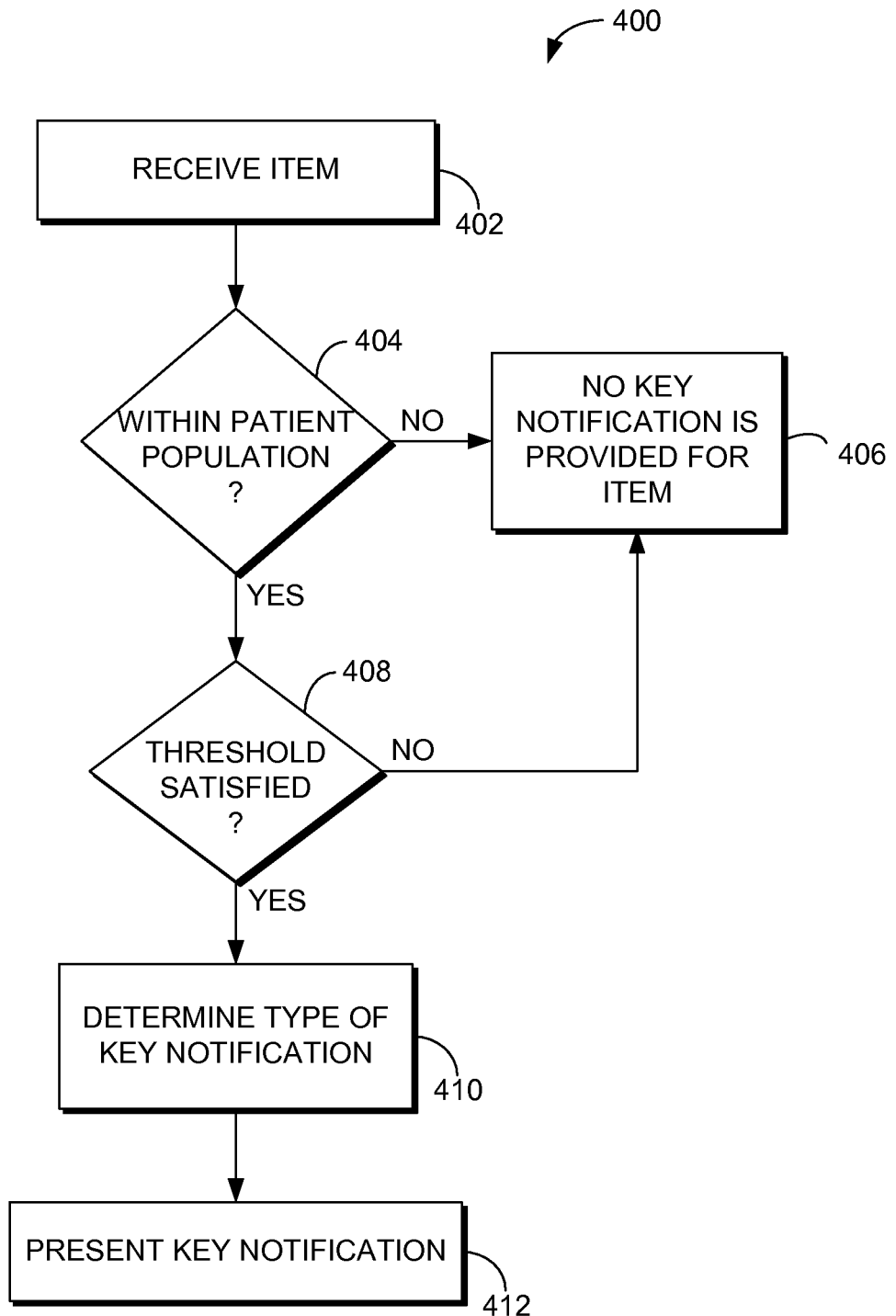
FIG. 4 is a flow diagram showing a method for providing a key notification in accordance with an embodiment of the present invention.

Referring now to FIG. 4, a flow diagram is provided illustrating an exemplary method 400 for providing a key notification to a clinician in accordance with an embodiment of the present invention. Initially, an item is received, as shown at block 402. The item may be any of a variety of different types of information that may be received by a clinical computing system for a clinician or pool of clinicians, such as a laboratory test result, a diagnostic test result, a message from another clinician, or an action item, for example. At block 404, a determination is made regarding whether the item is associated with a patient within a predefined patient population for which key notifications are to be provided. As indicated previously, embodiments of the present invention may filter items to be included in key notifications based on patient populations. If the item is not associated with a patient for which key notifications may be provided, no key notification is provided for the item, as shown at block 406.

If it is determined that the item is associated with a patient for which key notifications may be provided, whether a predefined threshold has been satisfied is determined, as shown at block 408. As discussed hereinabove, a variety of system-defined and/or user-defined thresholds may be established for determining whether a key notification should be provided for a particular item. If the item does not satisfy a predefined threshold, no key notification is provided, as shown at block 406. If the item does satisfy a predefined threshold, the type of key notification for the item may be determined, as shown at block 410. For example, in some embodiments, key notifications may be provided for critical items, abnormal items, and due items. In such embodiments, a determination is made as to whether the item qualifies as a critical item, abnormal item, or a due item. In some embodiments, such a determination may be made based on the same predefined thresholds used to determine whether a key notification should be provided for the item. In addition, in some embodiments, a user may receive separate sets of key notifications based on, for example, patient populations. In such embodiments, the item is also associated with the appropriate set of key notifications.

At block 412, a key notification is presented for the item. As discussed previously, the key notification may be presented via a key notification user interface. In some embodiments, the key notification user interface may be presented within an application in which the user is working. In other embodiments, the key notification user interface may be presented independently of any application, for example, via a separate pop-up window. Further, as noted above, visual, audible, and/or other types of alerts may be provided to direct the user's attention to the new key notification.

After receiving a key notification, a user may quickly access details of the item associated with the key notification and make a determination regarding what actions, if any, should be taken based on the information. In some cases, the user may require additional information regarding the patient, such as previous laboratory testing results, for example, to make an appropriate determination. Accordingly, because the key notifications may be associated with clinical computing systems having access to patient information, embodiments of the invention allow a user to quickly access necessary additional information. Further, embodiments of the present invention may also allow the user to resolve the item by presenting, in conjunction with the item and any additional information, clinical computing user interfaces, such as, for example, an order entry system. For instance, if a clinician determines based on the item and any additional information that certain medications should be prescribed, the clinician may access a medication order entry user interface to prescribe the medications.

Figure 5:
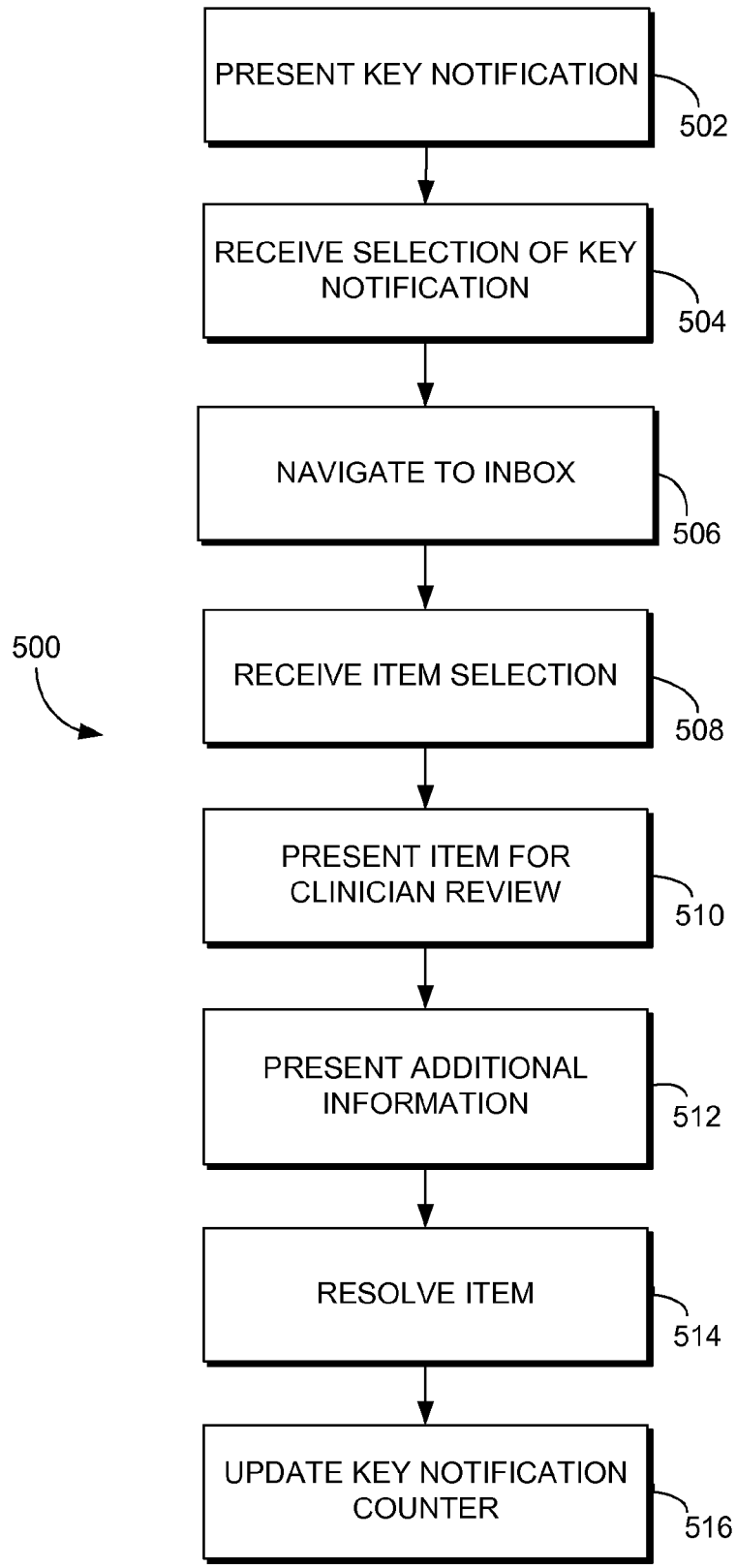
FIG. 5 is a flow diagram showing a method for accessing an item associated with a key notification and addressing the item in accordance with an embodiment of the present invention.

Referring to FIG. 5, a flow diagram is provided illustrating an exemplary method 500 for accessing an item associated with a key notification and addressing the item in accordance with an embodiment of the present invention. Initially, as shown at block 502, a key notification is presented via a key notification user interface. A clinician may recognize that a new key notification has been received and may select the key notification via the key notification user interface, as shown at block 504. In response to the user selection, the clinician may be directed (or navigated) to an inbox within the clinical computing system in which items for the clinician may be accessed, as shown at block 506. The clinician may review the items in the inbox and select the item corresponding with the key notification, as shown at block 508. The item is then presented for the clinician's review, as shown at block 510. In some cases, the clinician may require additional information, such as previous test results, to determine what actions, if any, should be taken in response to the item. Accordingly, additional information is presented for the clinician's review, as shown at block 512. After reviewing the key item and any additional information, the clinician may resolve the item, as shown at block 514. This may involve a variety of different actions within various embodiments of the present invention. By way of example only and not limitation, the clinician may access an order entry system and enter an order for the patient, such as an order for further testing or a medication prescription. As another example, the clinician may send a message to a nurse with instructions of any actions to be taken based on the key item. After the item has been addressed by the clinician, the counter associated with the key notification is updated to reflect that the item has been addressed, as shown at block 516.

In operation, an embodiment of the invention is now described by way of an example of a clinician receiving a key notification for a due item and addressing the due item. The example may be described with reference to FIGS. 6A through 6D, which illustrate a progression of exemplary screen displays in accordance with an embodiment of the present invention. It will be understood and appreciated by those of ordinary skill in the art that the screen displays of FIGS. 6A through 6D are provided by way of example only and are not intended to limit the scope of the present invention in any way.

In the present example, a clinician, Dr. John Jones, is examining a patient, Pamela Kohler in an exam room. The exam room includes a computing device through which Dr. Jones may access patient information via a clinical computing system. As shown in FIG. 6A, Dr. Jones has the patient chart for Pamela Kohler opened when a key notification for a due item is received via a key notification user interface 602. When Dr. Jones locates a cursor over the due item key notification 604, a dialog 606 is provided with information regarding the key notification. In the present example, a patient's name is provided. In embodiments of the invention, various levels of detail regarding key items may be provided in a dialog, such as the dialog 606. In addition, if a user has received multiple due items, the dialog may list each of the due items. In some embodiments, the list may be limited to a particular number, such as three items, in cases in which a user has received a large number of items.

Figure 6B:
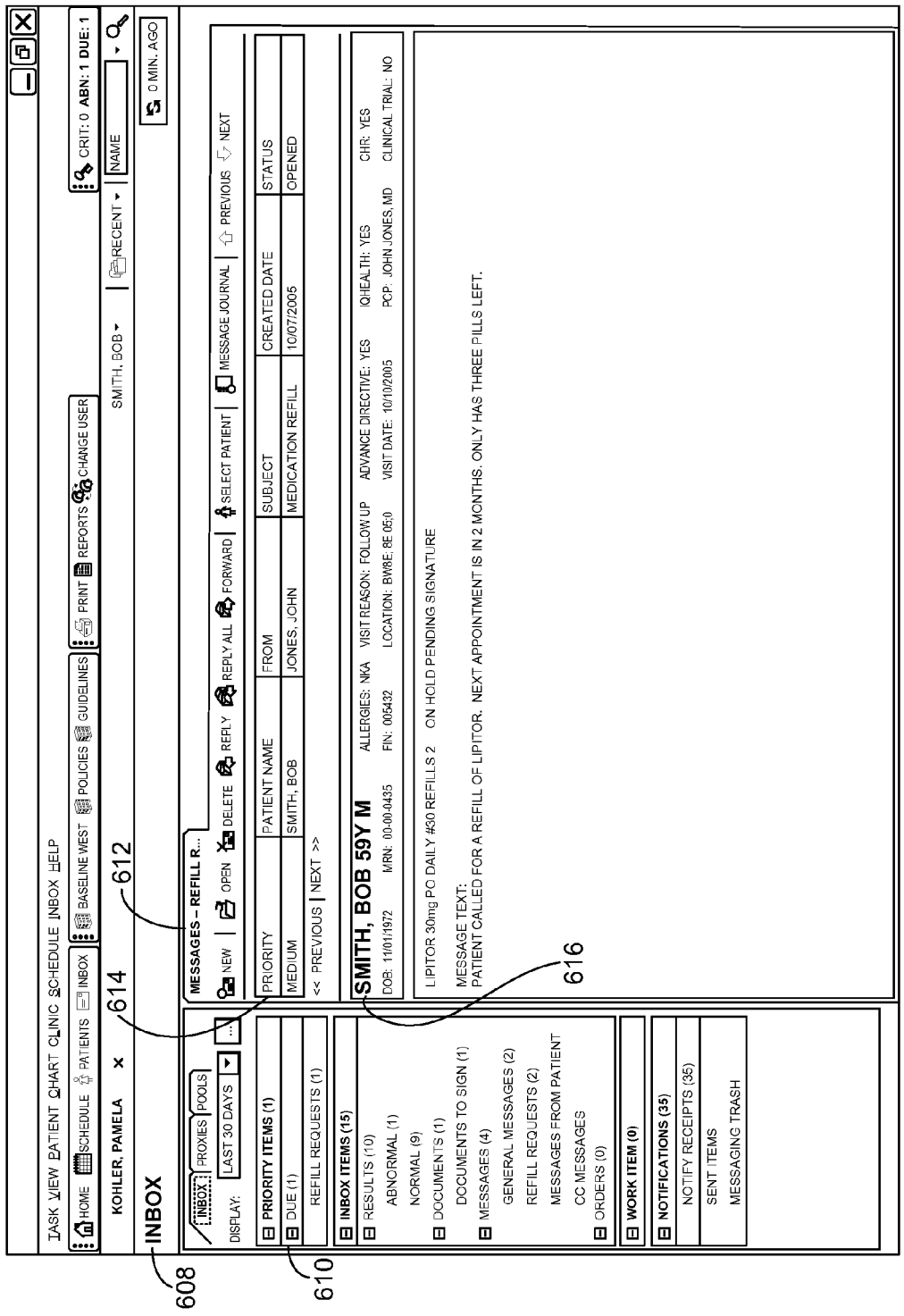

Dr. Jones selects the due item key notification 604, thereby navigating to Dr. Jones' inbox 608, as shown in the screen display of FIG. 6B. By selecting the due item key notification, Dr. Jones has been navigated directly to a view corresponding with due items 610 within Dr. Jones' inbox 608. The view includes a message summary area 612, which provides a list 614 of the various due items for Dr. Jones. As shown in FIG. 6B, Dr. Jones currently only has one due item. However, if Dr. Jones had multiple due items, each would be provided in the list 614. The message summary area 612 further includes a message preview area 616 providing a preview of the message for a selected due item.

Figure 6C:
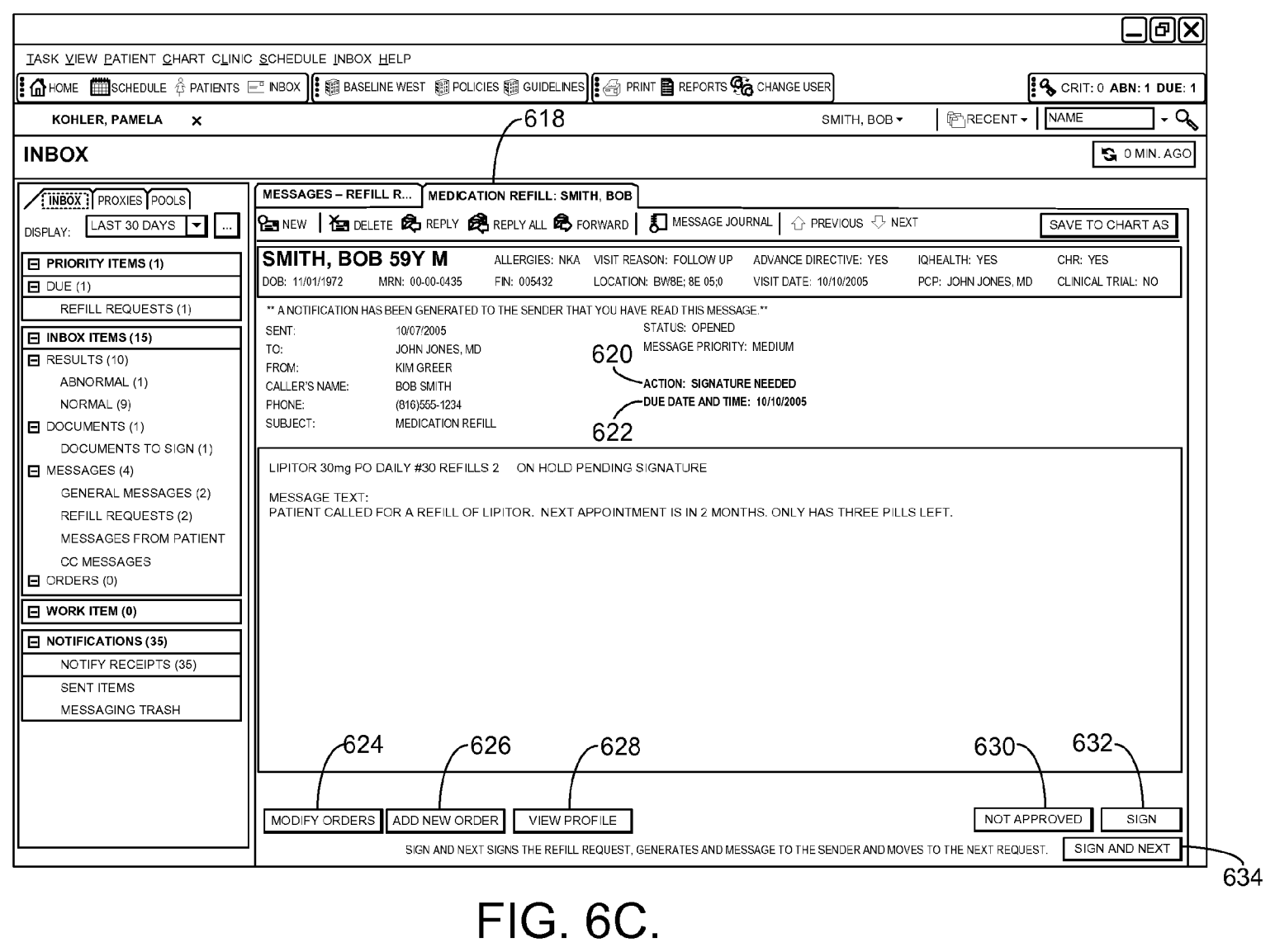
Figure 6D:
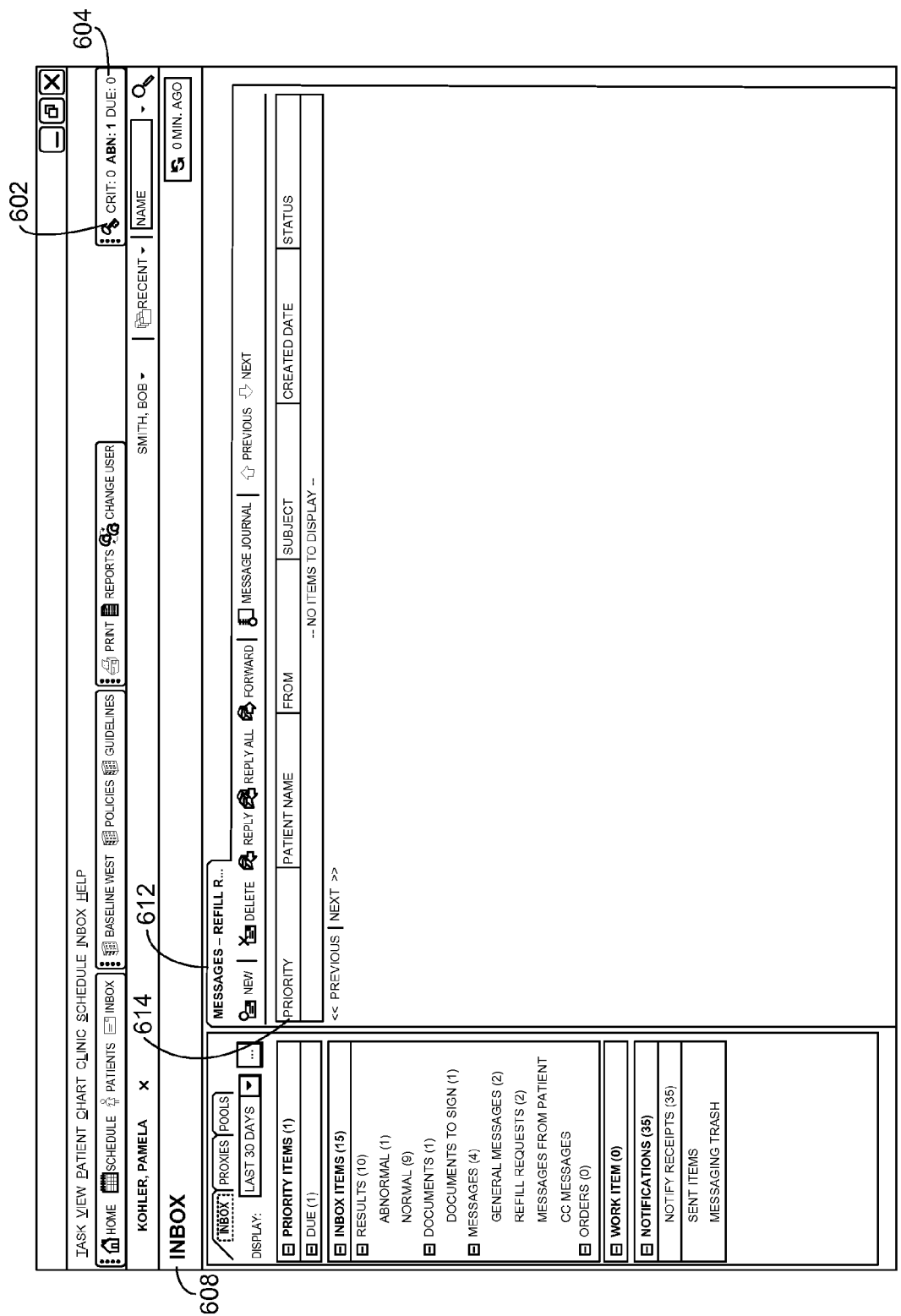

Dr. Jones decides to open the message associated with the due item, which is displayed in a message area 618, as shown in the screen display of FIG. 6C. As shown in FIG. 6C, the message indicates that a patient, Bob Smith, has called requesting a prescription for a refill of Lipitor. In addition, the message indicates that the action 620 associated with the due item is a signature for the prescription. The message further indicates a due date and time 622 for the due item. After reviewing the information, Dr. Jones may take a number of different actions via a series of action buttons 624, 626, 628, 630, 632, or 634 provided at the bottom of the message area 618. In the present example, Dr. Jones decides to sign the prescription by selecting the sign button 632. Accordingly, the corresponding due item is removed from the list 610 of due items within Dr. Jones' inbox 608, as shown in FIG. 6D. In addition, the key notification user interface 602 is updated to reflect that the due item has been addressed by clearing the counter associated with the due item key notification 604.

Another embodiment of the present invention is now described by way of an example in which a clinician receives a key notification for an abnormal item and addresses the abnormal item. The example is described with reference to FIGS. 7A through 7E, which illustrate exemplary screen displays in accordance with an embodiment of the present invention. It will be understood and appreciated by those of ordinary skill in the art that the screen displays of FIGS. 7A through 7E are provided by way of example only and are not intended to limit the scope of the present invention in any way.

Figure 7B:
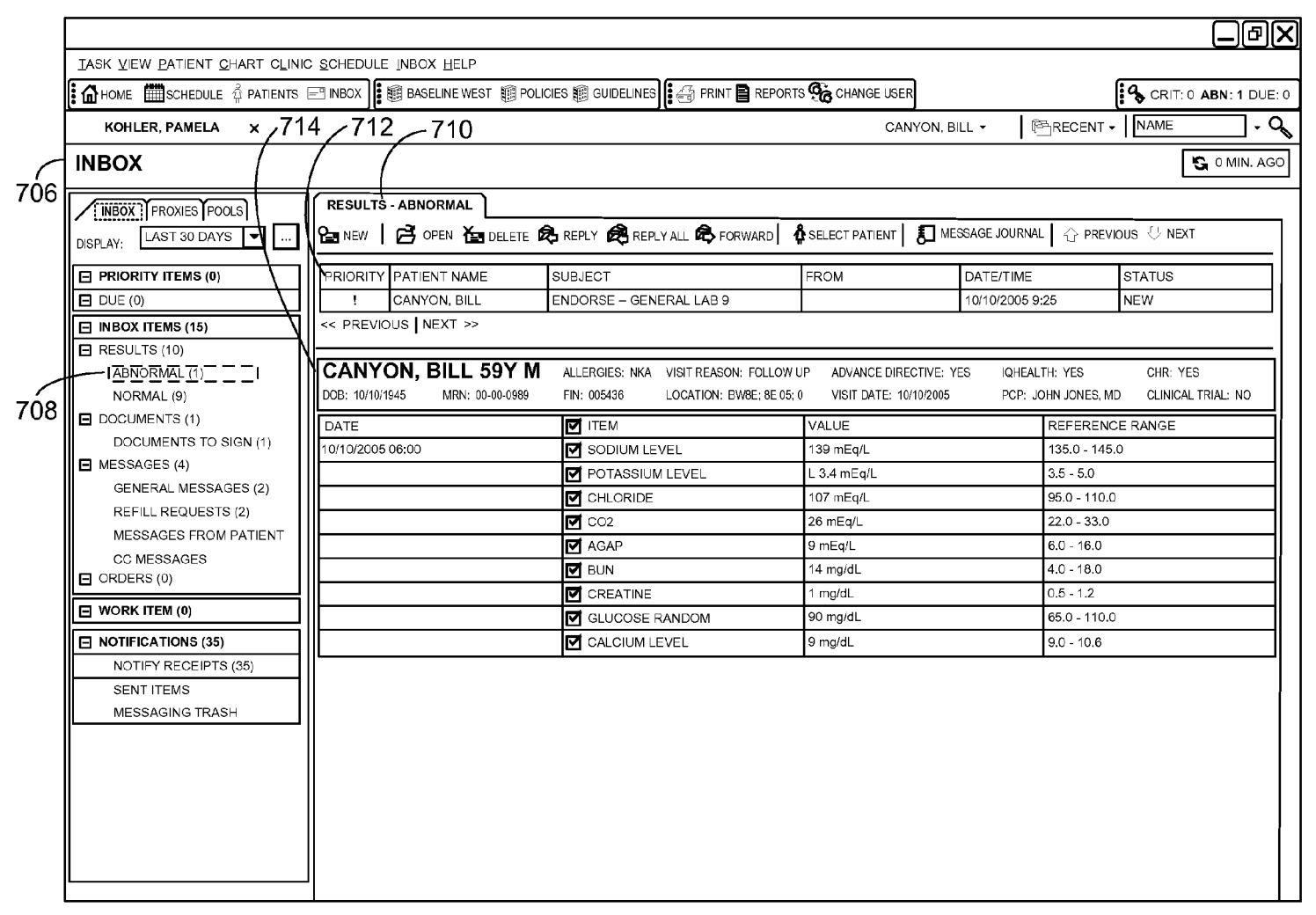

In the present example, Dr. Jones is reviewing the schedule when Dr. Jones receives an abnormal item key notification 704 via a key notification user interface 702, as shown in FIG. 7A. Dr. Jones selects the abnormal item key notification 704 and is navigated to Dr. Jones' inbox 706, as shown in FIG. 7B. In particular, Dr. Jones has been navigated directly to a view displaying abnormal items 708 within Dr. Jones' inbox 706. A results message area 710 is displayed providing a list 712 of abnormal items within Dr. Jones' inbox. As shown in FIG. 7B, there is currently only one abnormal item. Similar to that described above with respect to due items, if Dr. Jones had multiple abnormal items, each would be provided in the list 712. The results message area 710 further includes a message preview area 714, providing a preview of a message selected from the list 712.

Figure 7C:
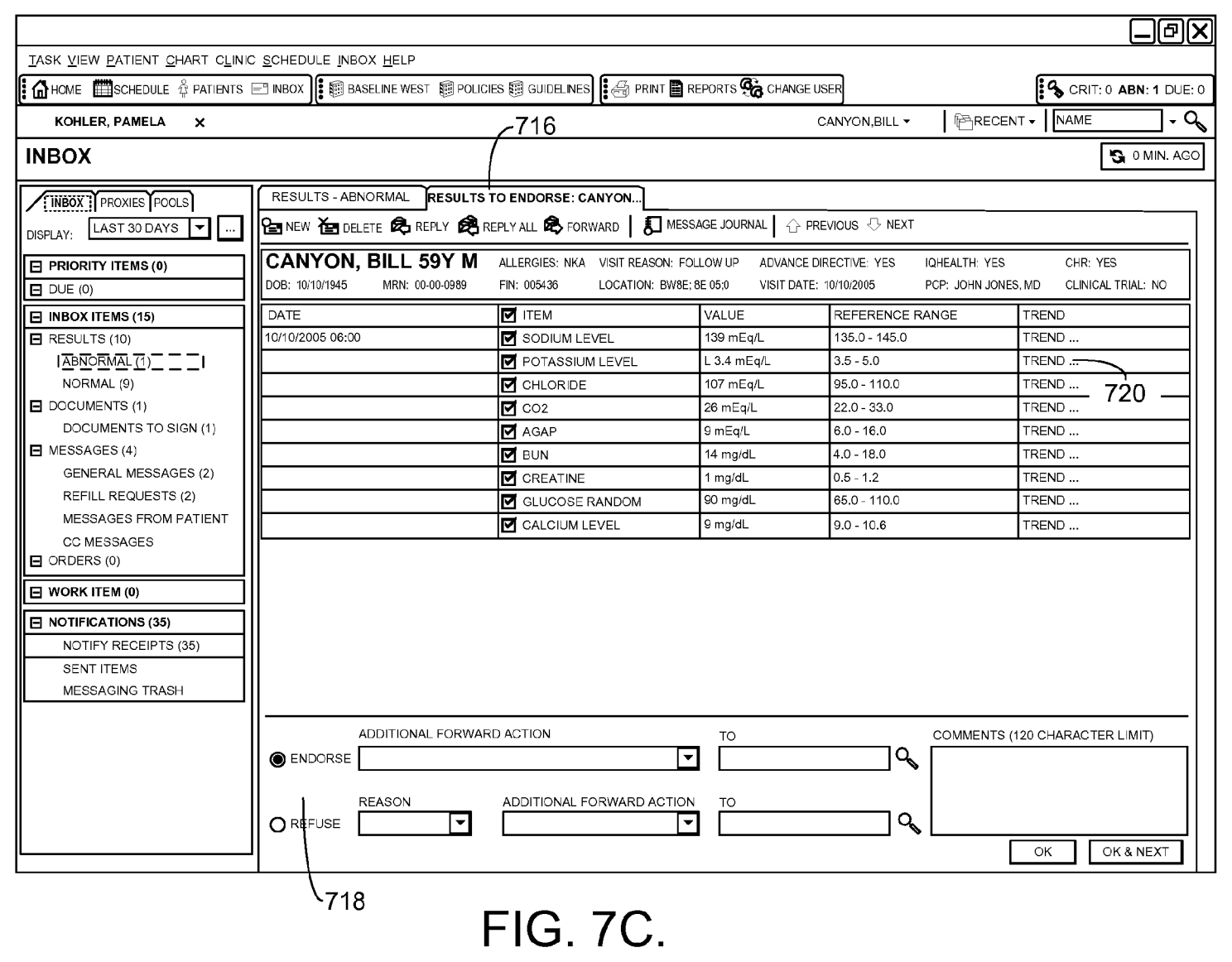

Dr. Jones selects to open the message for the abnormal item, which is displayed in a message area 716, as shown in FIG. 7C. The message area 716 includes laboratory results provided for the patient, Bill Canyon. Reference ranges are also provided for each test result. As shown in FIG. 7C, an action area 718 is also provided to allow Dr. Jones to indicate any actions that should be taken based on the abnormal item.

Figure 7D:
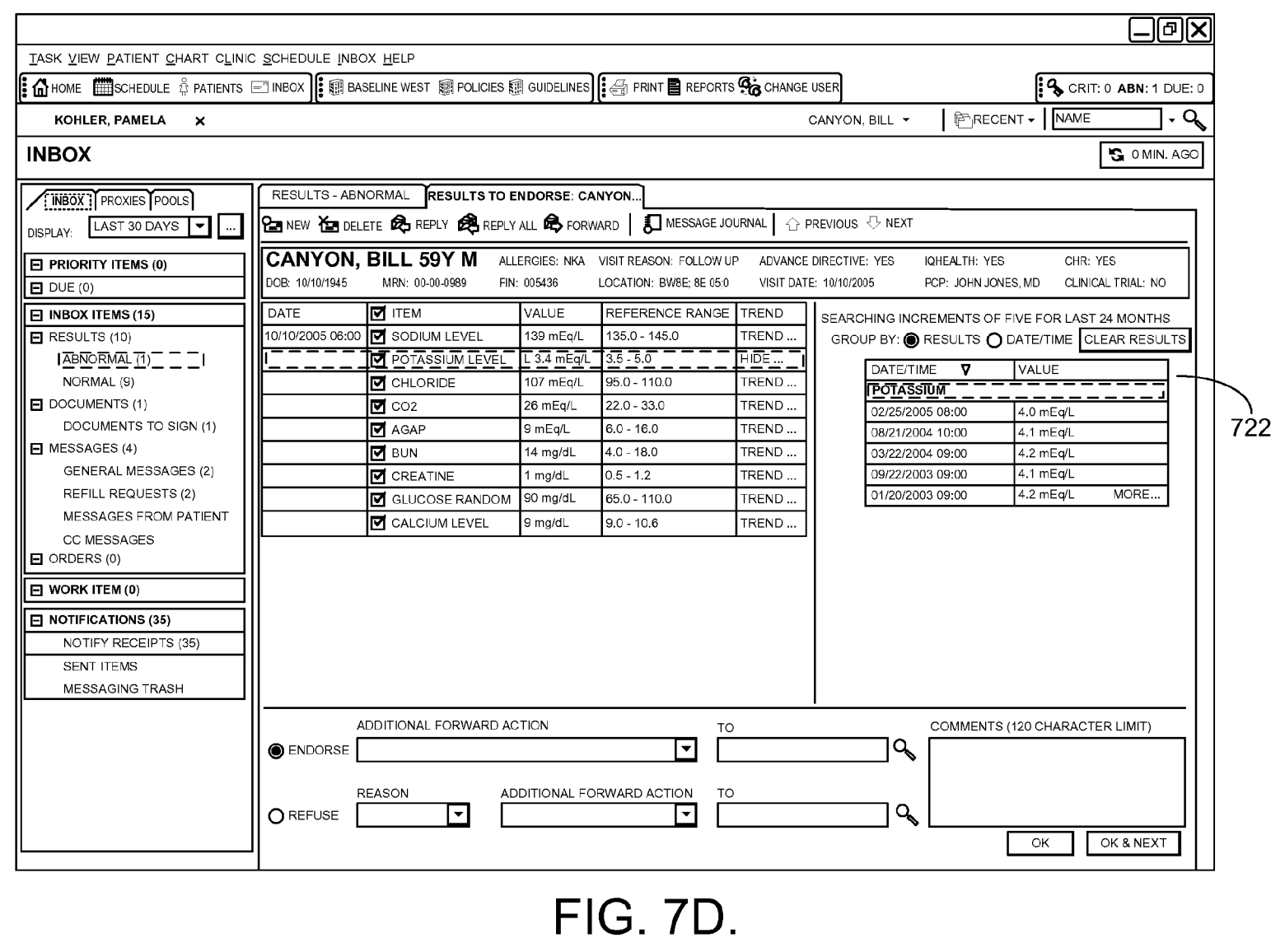

Reviewing the results, Dr. Jones recognizes that the patient's potassium value is outside of the corresponding reference range. In this case, Dr. Jones decides to view additional test results for the patient by selecting the trend 720 for potassium. In response to the selection, a history 722 of potassium results for the patient is provided, as shown in FIG. 7D. The additional information may assist Dr. Jones in determining what course of action would be appropriate for the patient based on the abnormal result. After reviewing the information, Dr. Jones decides that the patient should be called for a follow-up. Accordingly, as shown in FIG. 7E, Dr. Jones indicates the action to be taken in the action area 718, including comments and instructions for the patient follow-up.

Referring now to FIGS. 8A through 8E, another embodiment of the present invention may described by way of example. The present example illustrates a clinician, Dr. Jones, receiving a critical result and addressing the critical result. It will be understood and appreciated by those of ordinary skill in the art that the screen displays of FIGS. 8A through 8E are provided by way of example only and are not intended to limit the scope of the present invention in any way.

Figure 8A:
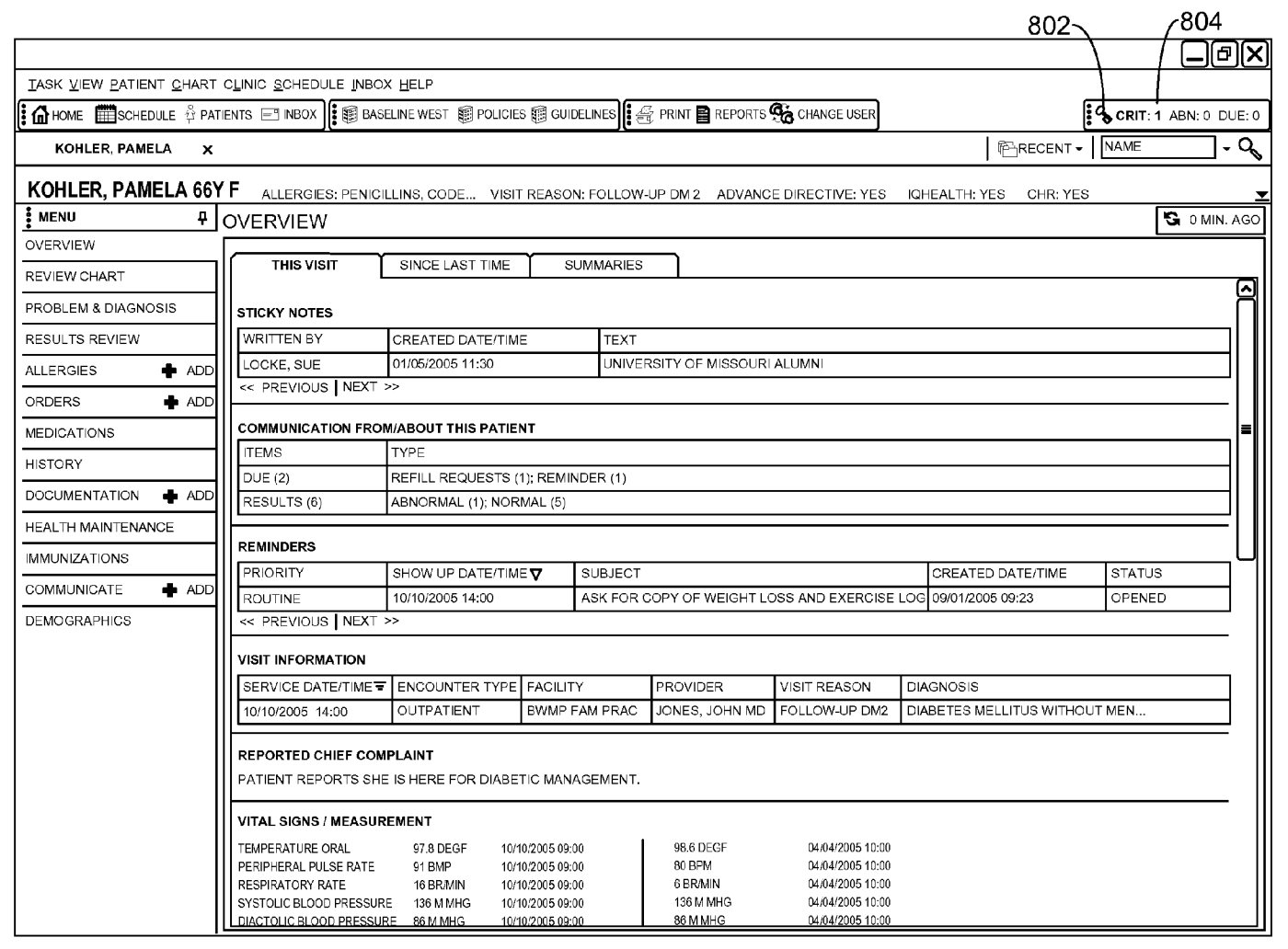
Figure 8B:
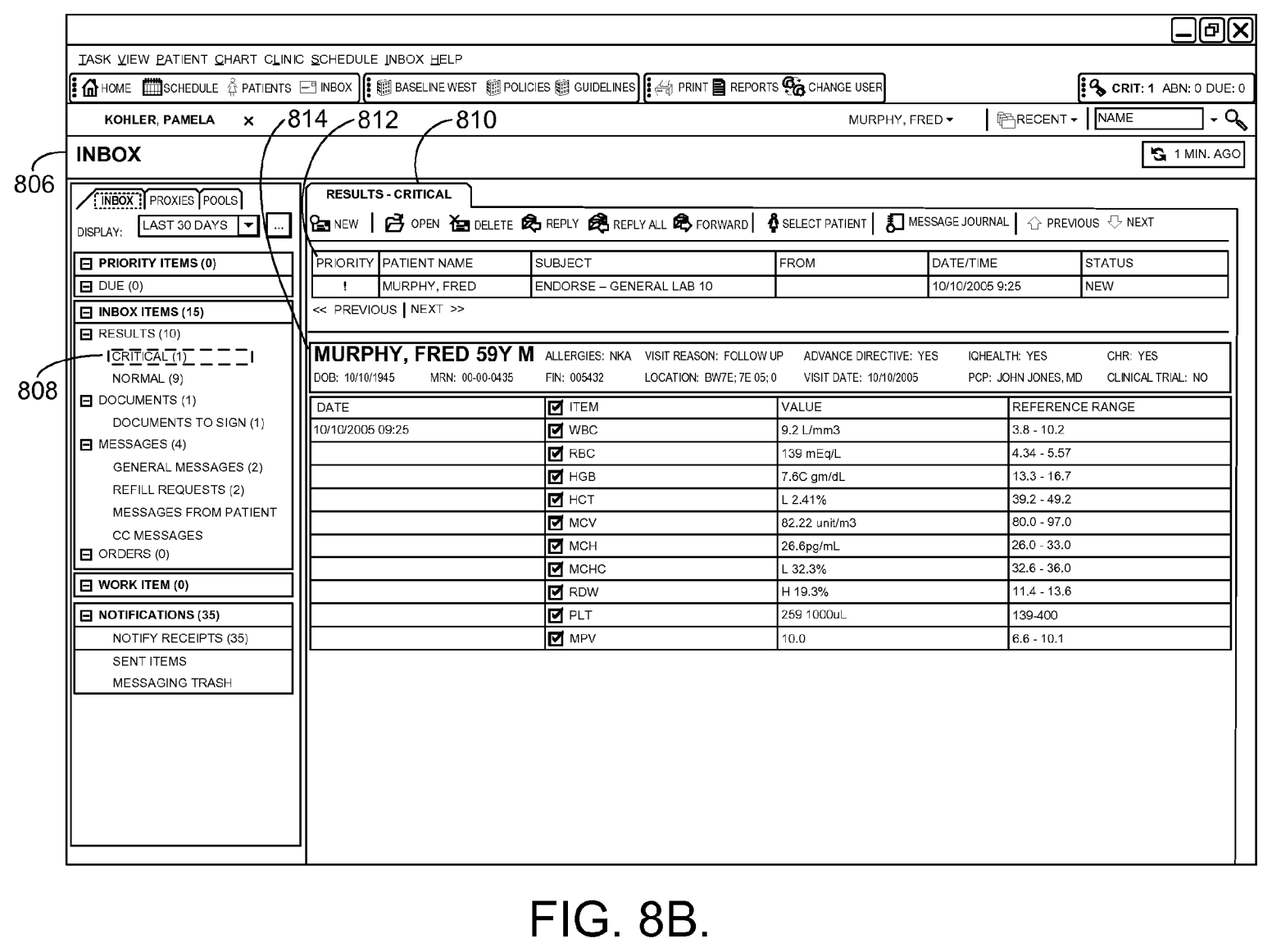

In the present example, Dr. Jones is visiting with a patient, Pamela Kohler, and is currently viewing the patient chart for Ms. Kohler. As shown in FIG. 8A, Dr. Jones receives a critical item key notification 804 via a key notification user interface 802. By selecting the critical item key notification 804, Dr. Jones is navigated to Dr. Jones' inbox 806, as shown in FIG. 8B. In particular, Dr. Jones has been navigated directly to a view displaying critical items 808 within Dr. Jones' inbox 806. A results message area 810 is displayed providing a list 812 of critical items within Dr. Jones' inbox. As shown in FIG. 8B, there is currently only one critical item. Similar to that described above with respect to due items and abnormal items, if Dr. Jones had multiple critical items, each would be provided in the list 812. The results message area 810 further includes a message preview area 814, providing a preview of a message selected from the list 812.

Dr. Jones selects to open the message for the critical item, which is displayed in a message area 816, as shown in FIG. 8C. The message area 816 includes laboratory results provided for the patient, Fred Murphy. Reference ranges are also provided for each test result. As shown in FIG. 8C, an action area 818 is also provided to allow Dr. Jones to indicate any actions that should be taken based on the critical item.

Figure 8D:
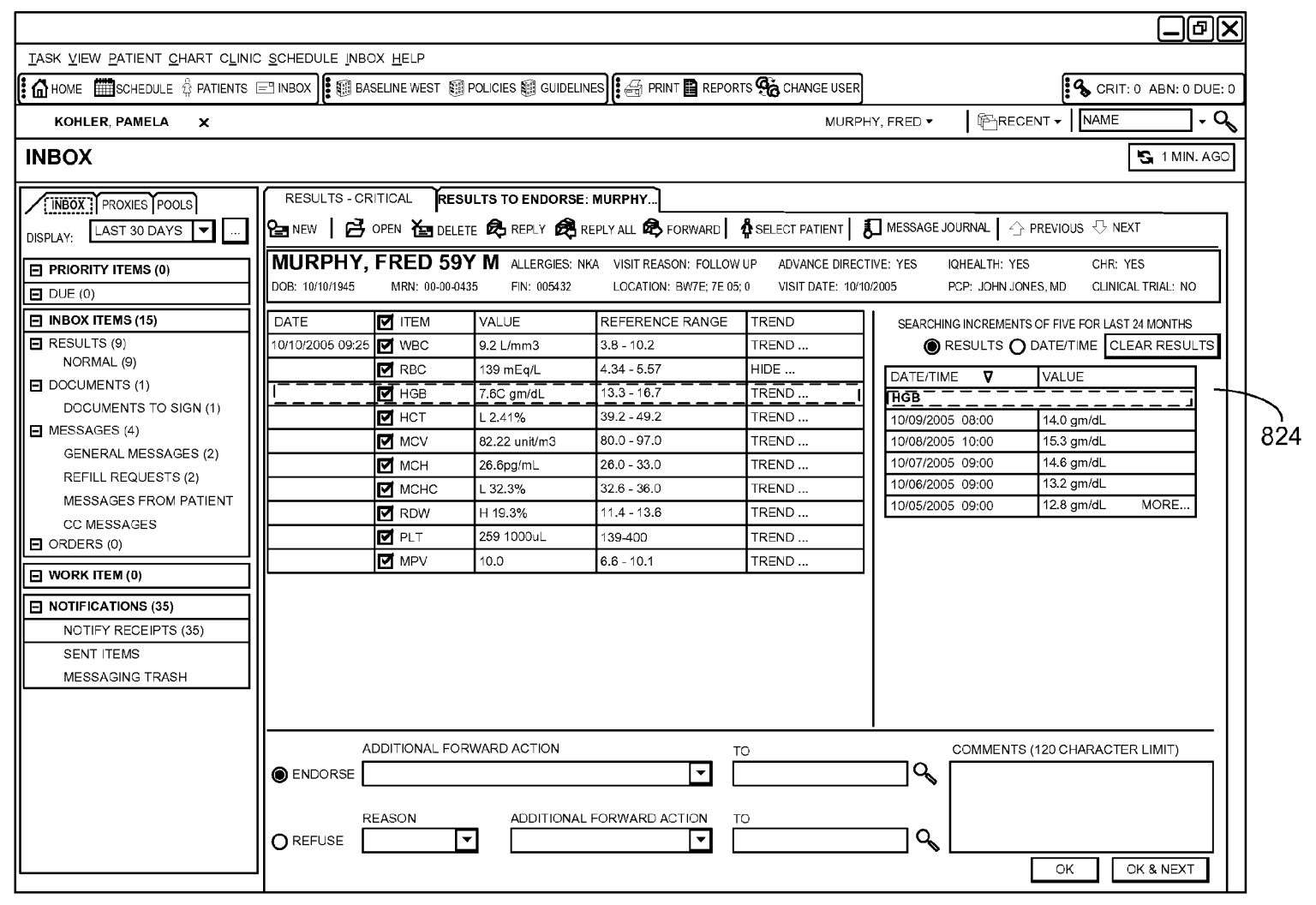
Figure 8E:
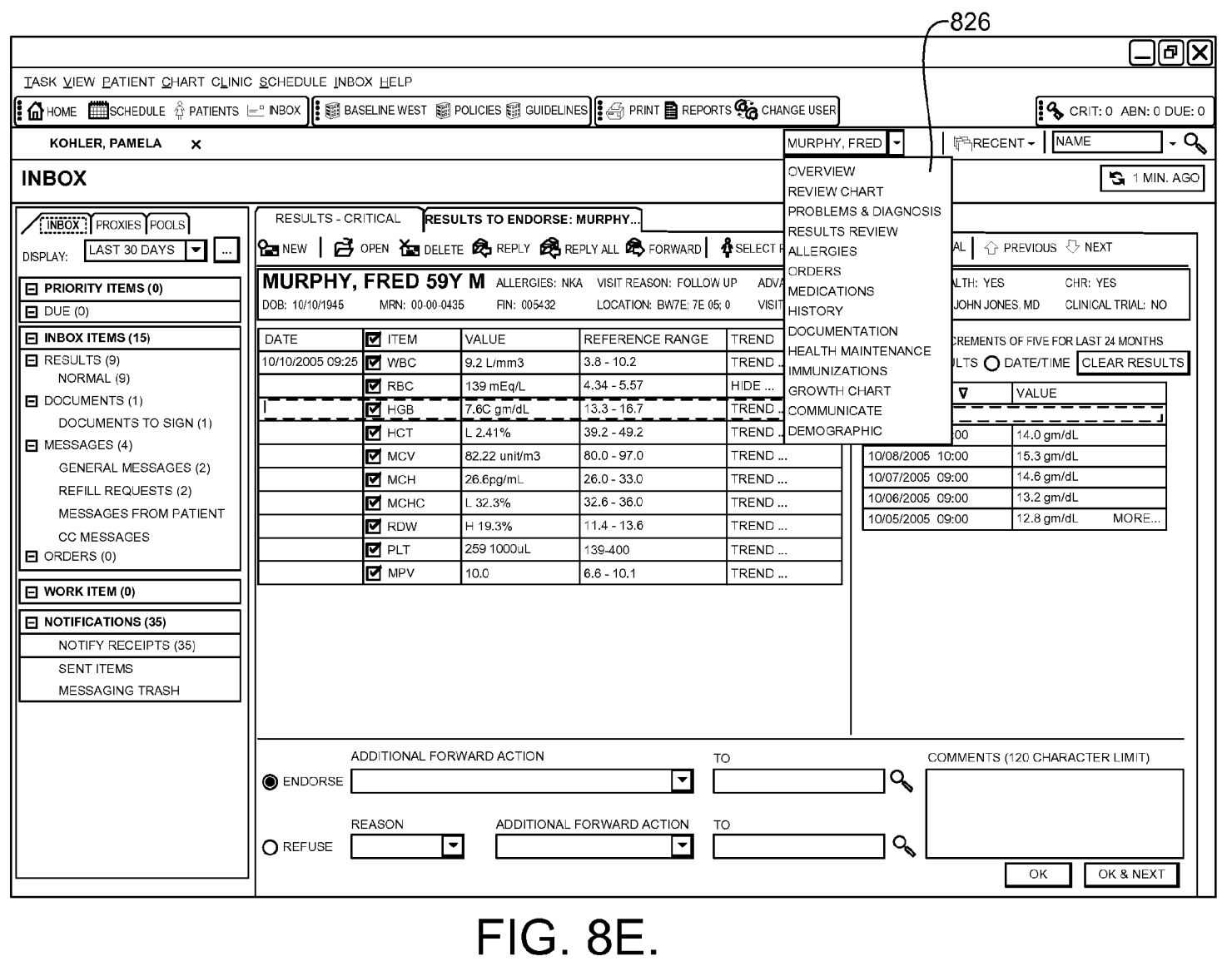

By reviewing the results, Dr. Jones recognizes that the patient has a critical result for hemoglobin, as indicated at 820. In the present embodiment, the critical result has been bolded, such that Dr. Jones may quickly recognize the critical result. Similar to that discussed with an abnormal result, Dr. Jones may view additional information for the patient by selecting the trend 822 for hemoglobin. Accordingly, a history 824 of hemoglobin results for the patient is provided, as shown in FIG. 8D. In some cases, Dr. Jones may wish to access additional information and/or take specific actions with respect to the patient. Accordingly, a drop down menu 826 is provided as shown in FIG. 8E, allowing Dr. Jones to quickly navigate into the patient's chart and take appropriate actions, such as initiating an order for the patient based on the critical result.

As can be understood, embodiments of the present invention provide systems, methods, and user interfaces for automatically triaging information in clinical settings by communicating electronic notifications to clinicians for key items determined to satisfy predefined criteria for criticality and time-sensitivity. Embodiments of the present invention further allow clinicians to quickly access and address the key items. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage devices storing computer-usable instructions that, when used by one or more computing devices, cause the one or more computing devices to perform a method in a clinical computing environment for automatically triaging one or more items of patient information, the method comprising:

identifying a plurality of patients associated with a clinician;

receiving the one or more items of patient information, wherein the one or more items of patient information are associated with the plurality of patients associated with the clinician;

filtering the one or more items of patient information based on a predetermined list of patients to provide a filtered set of patient information, wherein the predetermined list of patients comprises a subset of the plurality of patients for which the clinician has indicated a request to receive a key notification, and wherein the filtered set of patient information comprises one or more items of patient information for one or more patients included in the predetermined list of patients;

identifying at least one of the one or more items of patient information in the filtered set of patient information as a time-sensitive item by identifying the at least one of the one or more items of patient information in the filtered set of patient information as requiring attention by a clinician by a particular time, wherein identifying the at least one of the one or more items of patient information in the filtered set of patient information as requiring attention by the clinician by the particular time comprises comparing the one or more items of patient information in the filtered set of patient information against one or more predetermined criteria for patients included in the predetermined list of patients, the one or more predetermined criteria having one or more predefined thresholds for time-sensitivity, wherein the one or more predetermined criteria are based at least in part on the predetermined list of patients, wherein the one or more predefined thresholds includes at least one of the following:

(1) one or more system-defined thresholds for the clinical computing environment, wherein the one or more system-defined thresholds are based on standard practices within at least one of a healthcare industry, a particular clinical facility, and a particular healthcare system, and (2) one or more user-defined thresholds for the clinical computing environment, wherein each of the one or more user-defined thresholds includes a plurality of rules for determining whether the key notification should be presented for the at least one of the one or more items of patient information in the filtered set of patient information identified as the time-sensitive item; and automatically presenting the key notification for the time-sensitive item, wherein the key notification provides notification of key information to the clinician, the key information including information regarding the identified at least one item of time-sensitive information, wherein the key notification corresponds with the predetermined list of patients.

2. The one or more computer storage devices of claim 1, wherein receiving the one or more items of patient information comprises receiving the one or more items of patient information at a user inbox within a clinical computing system.

3. The one or more computer storage devices of claim 1, wherein the one or more items of patient information comprise at least one of a laboratory testing result, a diagnostic testing result, an electronic mail message, and a due item.

4. The one or more computer storage devices of claim 1, wherein identifying the at least one of the one or more items of patient information as the time-sensitive item comprises filtering the one or more items of patient information based on the predetermined criteria.

5. The one or more computer storage devices of claim 1, wherein the one or more predetermined criteria are based at least in part on patient characteristics.

6. The one or more computer storage devices of claim 1, wherein the one or more user-defined thresholds comprise at least one of a global threshold and a patient-specific threshold.

7. The one or more computer storage devices of claim 1, further comprising determining the time-sensitive item as at least one of a critical item, an abnormal item, and a due item.

8. The one or more computer storage devices of claim 1, wherein the key notification is provided independent of a user inbox within the clinical computing environment.

9. The one or more computer storage devices of claim 1, wherein the key notification is provided independent of a patient chart for a patient corresponding with the time-sensitive item.

10. The one or more computer storage devices of claim 1, further comprising allowing a user to address the time-sensitive item.

11. The one or more computer storage devices of claim 10, wherein allowing a user to address the time-sensitive item comprises:
  receiving a user selection of the key notification;
  accessing the time-sensitive item in response to the user selection of the key notification; and
  presenting the time-sensitive item.

12. The one or more computer storage devices of claim 11, wherein allowing a user to address the time-sensitive item further comprises:
  receiving a request for additional patient information;
  accessing the additional patient information; and
  presenting the additional patient information.

13. A system in a clinical computing environment for automatically triaging one or more items of patient information, the system comprising:
  a computing device having a processor and a memory, wherein the computing device comprises:
    an item receiving component for receiving the one or more items of patient information, wherein the one or more items of patient information are associated with patients of a clinician;
    an identification component for identifying at least one of the one or more items of patient information as a time-sensitive item, wherein identifying the at least one of the one or more items of patient information as the time-sensitive item comprises identifying the item as requiring attention by the clinician by a particular time by utilizing at least one user-defined threshold for the clinical computing environment that is customized for a patient that is categorized in a particular patient population, wherein each of the at least one user-defined thresholds is customized based on a defined list of patient characteristics for patients belonging to the particular patient population, and further wherein each of the at least one user-defined thresholds includes a plurality of rules for determining whether a key notification should be presented for the at least one of the one or more items of patient information identified as the time-sensitive item; and
  a key notification component for automatically presenting the key notification for the time-sensitive item, wherein the key notification provides notification of key information to the clinician, the key information including information regarding the identified at least one time-sensitive item of patient information.

14. One or more computer storage devices having computer-useable instructions embodied thereon that provide for a presentation of one or more user interfaces for triaging patient information in a clinical computing environment, the one or more user interfaces comprising:
  a key notification area configured to display one or more key notifications to a user, each of the one or more key notifications corresponding with one or more items of patient information determined to satisfy predefined criteria for time-sensitivity, the one or more items of patient information determined to satisfy the predefined criteria for time-sensitivity including a critical item, an abnormal item, and a due item, and the one or more key notifications providing notification of information regarding the one or more items of patient information determined to satisfy the predefined criteria for time-sensitivity, wherein time-sensitivity refers to requiring attention by the user by a particular time, and further wherein the predefined criteria for time-sensitivity comprise a patient population criterion, a system-defined threshold for time-sensitivity for the clinical computing environment, and a user-defined threshold for time-sensitivity for the clinical computing environment, wherein:
    the patient population criterion indicates a category of patients that are a subset of a plurality of patients associated with the user,
    the system-defined threshold for time-sensitivity is based on standard practices within at least one of a healthcare industry, a particular clinical facility, and a particular healthcare system, and
    the user-defined threshold for time-sensitivity includes a plurality of rules for determining whether the one or more key notifications should be presented.

15. The one or more computer storage devices of claim 14, wherein each of the one or more key notifications allows the user to navigate to corresponding one or more items of patient information.

* * * * *